United States Patent
Frischke et al.

(10) Patent No.: US 11,975,183 B2
(45) Date of Patent: May 7, 2024

(54) COMPONENT FOR CONDUCTING A FLUID HAVING A SENSOR

(71) Applicant: Berlin Heart GmbH, Berlin (DE)

(72) Inventors: Michael Frischke, Rangsdorf (DE); Daniel Phillips, Berlin (DE); Oliver Peters, Berlin (DE); Valentin Bykov, Berlin (DE); Florian Jankowsky, Friedland (DE)

(73) Assignee: Berlin Heart GmbH, Berlin (DE)

( * ) Notice: Subject to any disclaimer, the term of this patent is extended or adjusted under 35 U.S.C. 154(b) by 738 days.

(21) Appl. No.: 17/057,049

(22) PCT Filed: May 27, 2019

(86) PCT No.: PCT/EP2019/063685
§ 371 (c)(1),
(2) Date: Nov. 19, 2020

(87) PCT Pub. No.: WO2019/224401
PCT Pub. Date: Nov. 28, 2019

(65) Prior Publication Data
US 2021/0361931 A1    Nov. 25, 2021

(30) Foreign Application Priority Data
May 25, 2018 (EP) .................................. 18174341

(51) Int. Cl.
*A61M 60/403* (2021.01)
*A61M 60/122* (2021.01)
(Continued)

(52) U.S. Cl.
CPC ........ *A61M 60/403* (2021.01); *A61M 60/122* (2021.01); *A61M 60/148* (2021.01);
(Continued)

(58) Field of Classification Search
CPC .......................... A61M 60/403; A61M 60/816
See application file for complete search history.

(56) References Cited

U.S. PATENT DOCUMENTS

| 6,367,333 B1 | 4/2002 | Bullister et al. |
| 2017/0112988 A1 | 4/2017 | Rosenberg et al. |
| (Continued) | | |

FOREIGN PATENT DOCUMENTS

EP    3 222 206 A1    9/2017

OTHER PUBLICATIONS

International Search Report with English translation, issued in International Application No. PCT/EP2019/063685, dated Aug. 1, 2019, pp. 1-6, European Patent Office, Rijswijk, Netherlands.

Primary Examiner — Matthew W Schall
(74) Attorney, Agent, or Firm — Crowell & Moring LLP

(57) ABSTRACT

A component for conducting a fluid having a sensor, wherein the component comprises an inner and an outer wall, wherein the inner wall is configured to conduct the fluid, the outer wall terminates the component to the outside, and a wall region is formed between the inner and outer walls. The component in accordance with the invention is characterized in that the sensor has an electromechanical element and is arranged in the wall region at the inner wall, wherein the sensor is adapted to measure a degree of deformation of the inner wall in the region of the sensor by means of the sensor element and to output it as an electrical signal, wherein the sensor element preferably has a length and/or a width of ≤50 µm.

15 Claims, 13 Drawing Sheets

(51) Int. Cl.
*A61M 60/148* (2021.01)
*A61M 60/165* (2021.01)
*A61M 60/216* (2021.01)
*A61M 60/523* (2021.01)
*A61M 60/531* (2021.01)
*A61M 60/546* (2021.01)
*A61M 60/554* (2021.01)
*A61M 60/816* (2021.01)
*A61M 60/857* (2021.01)

(52) U.S. Cl.
CPC ........ *A61M 60/165* (2021.01); *A61M 60/216* (2021.01); *A61M 60/523* (2021.01); *A61M 60/531* (2021.01); *A61M 60/546* (2021.01); *A61M 60/554* (2021.01); *A61M 60/816* (2021.01); *A61M 60/857* (2021.01); *A61M 2205/3327* (2013.01); *A61M 2207/00* (2013.01)

(56) References Cited

U.S. PATENT DOCUMENTS

2017/0348470 A1    12/2017   D'Ambrosio et al.
2018/0085505 A1     3/2018   Casas a)

b)

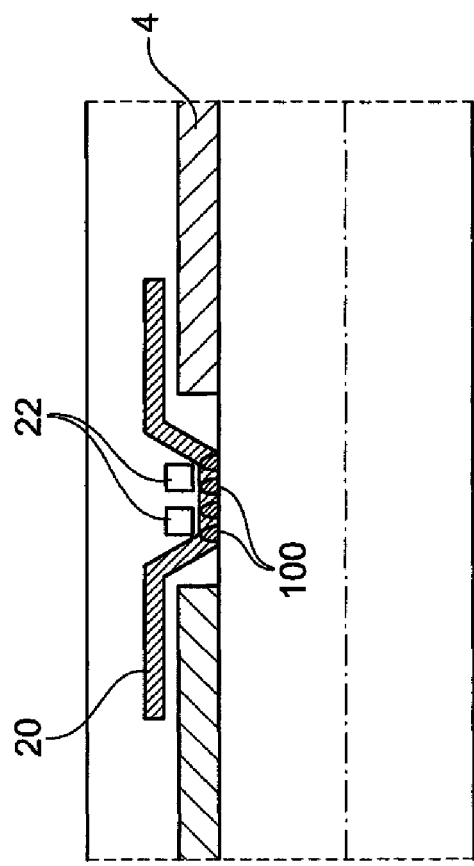
Fig. 3c
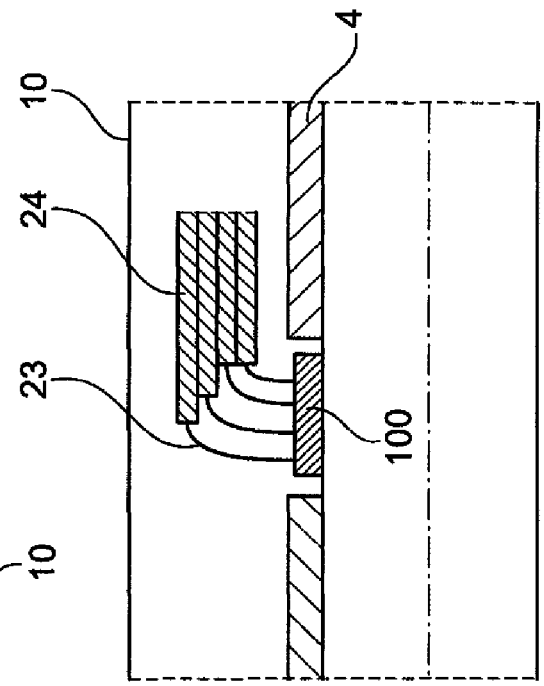
Fig. 3d
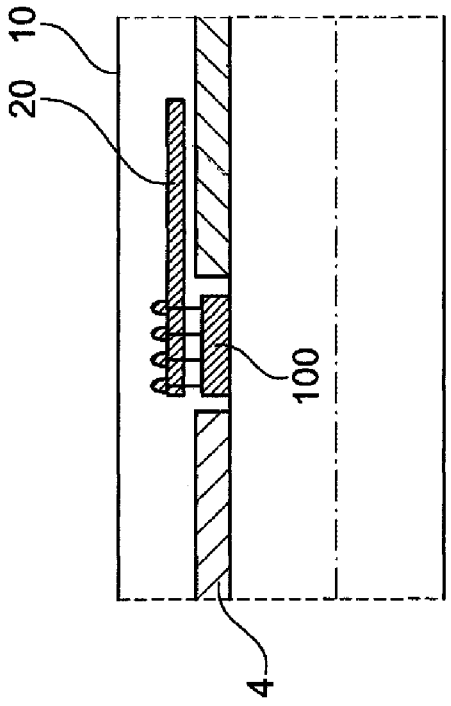

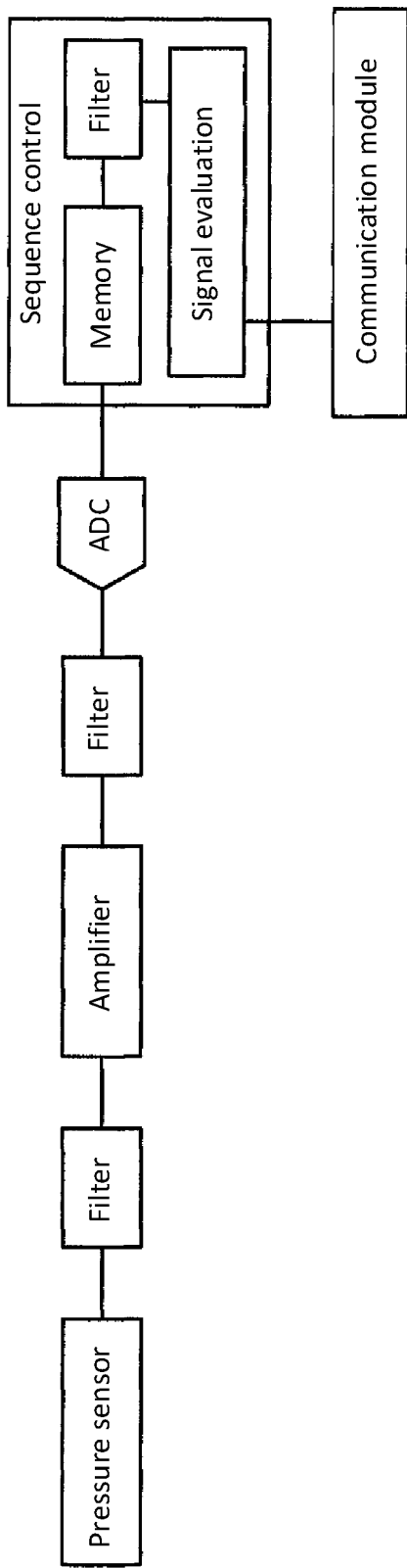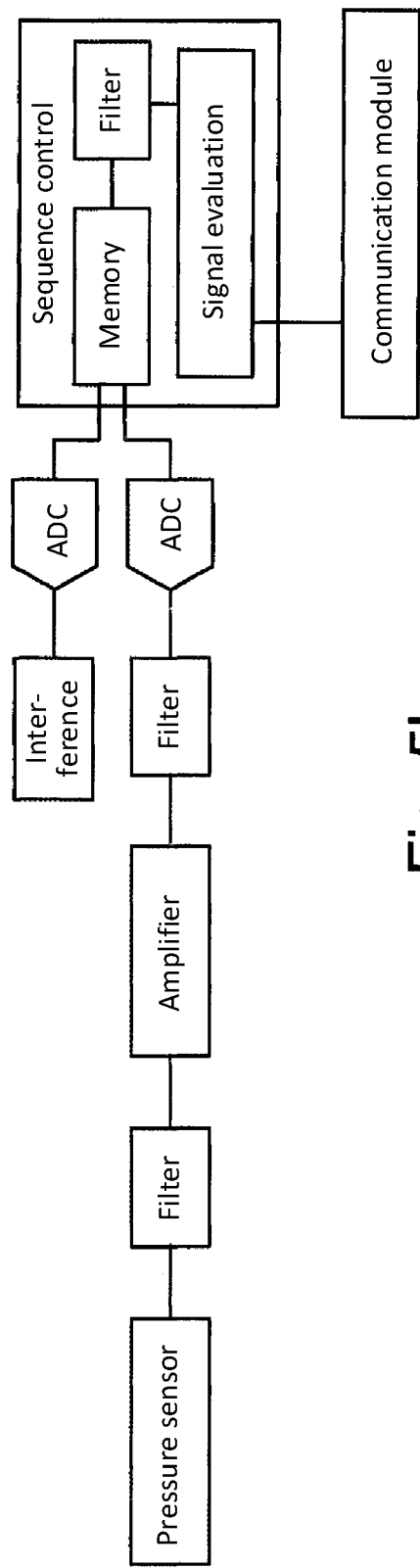
Fig. 5a
Fig. 5b

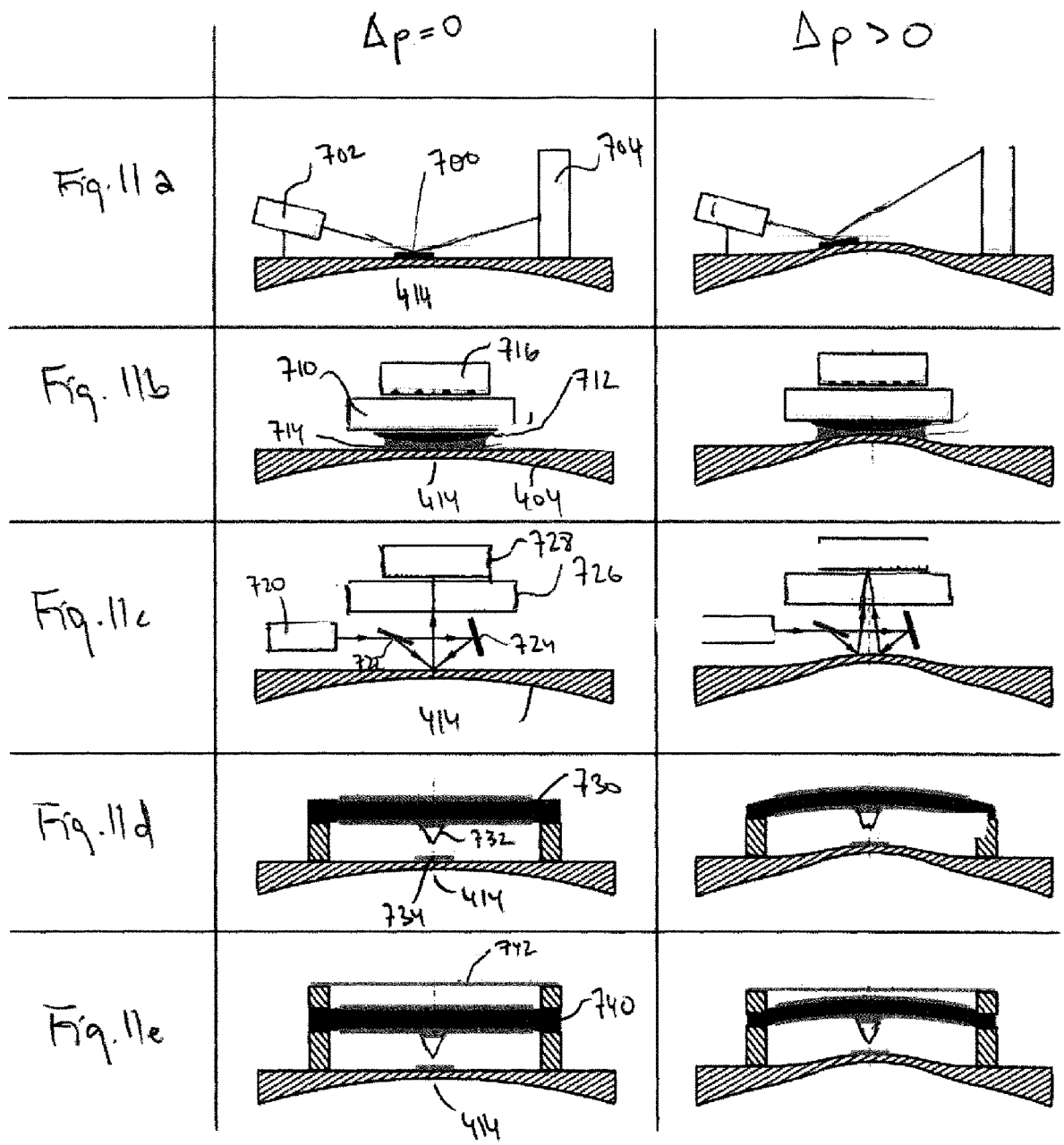

COMPONENT FOR CONDUCTING A FLUID HAVING A SENSOR

CROSS-REFERENCE TO RELATED APPLICATIONS

This application is a 371 nationalization of international patent application PCT/EP2019/063685 filed May 27, 2019, which claims priority under 35 USC § 119 to European patent application 18174341.0 filed May 25, 2018. The entire contents of each of the above-identified applications are hereby incorporated by reference.

BRIEF DESCRIPTION OF THE DRAWINGS

There are shown:

FIGS. 3a to 3g different variants for the electrical connection of a sensor in a blood pump tube;

FIGS. 5a to 5f different variants of signal chains from one or more sensors to a communication module;

FIGS. 11a to 11e further exemplary sensor arrangements.

DETAILED DESCRIPTION

Figure 1:
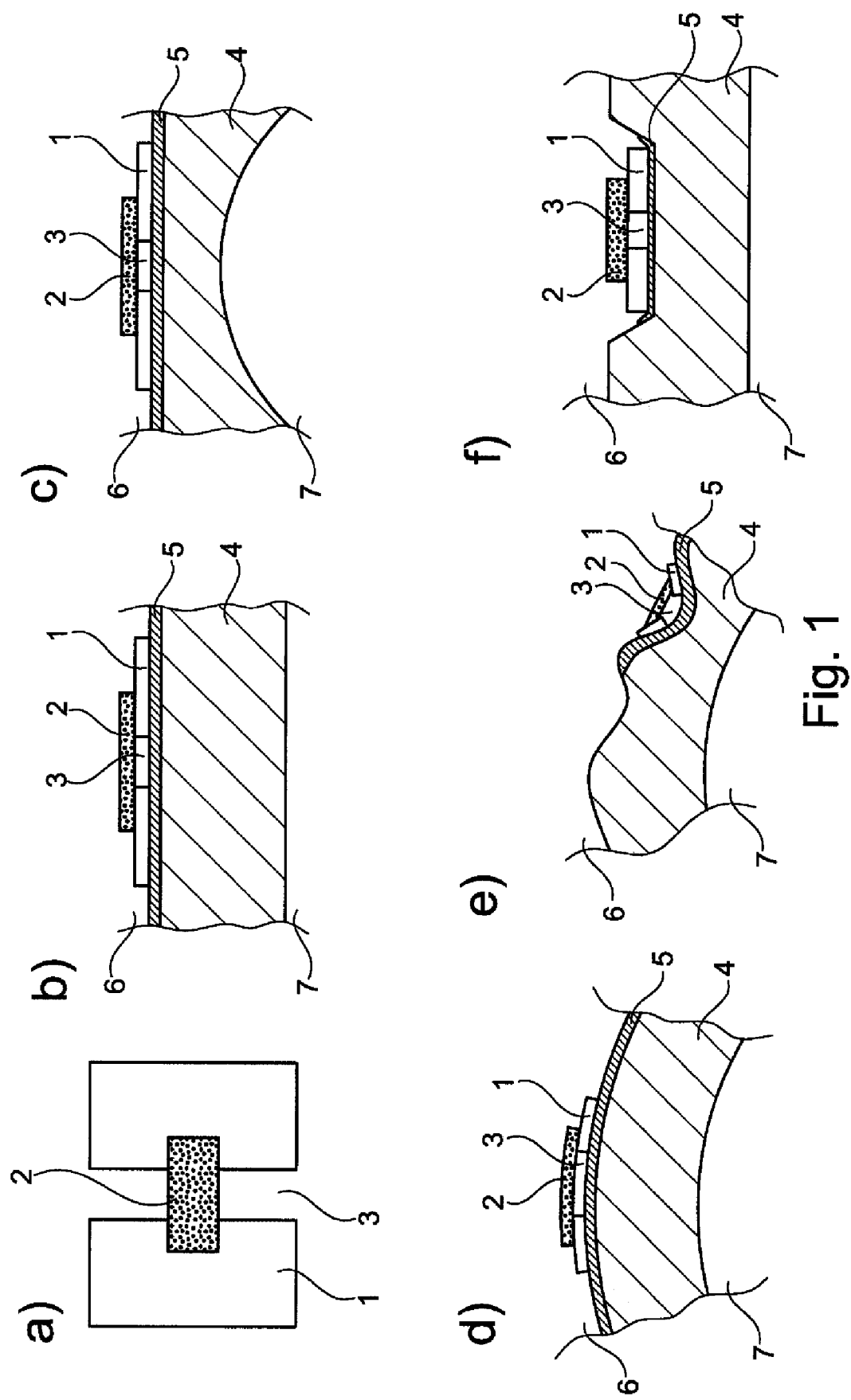
FIGS. 1a to 1c a plan view of a part of a sensor; a sensor application at different variants of an inner wall of differing geometries.

The present invention relates to a component for conducting a fluid having a sensor for measuring a deformation of the component. The invention further relates to a method of manufacturing the component comprising the sensor. The respective component can in particular be used in the field of heart assist systems.

In the field of heart assist systems in today's state of the art, the demands on the sensor system to be integrated have increased and are increasingly gaining importance in modern heart assist systems to be able to care for and support a patient reliably and in accordance with the individual support requirements. Primarily those demands are meant that permit a blood compatible and simultaneously reliable measurement of different parameters (e.g. pressure measurement, flow measurement, material fatigue, vibration measurement, abutment detection, detection of a thrombi passage, detection and distinction of systematic and random interference variables).

Currently a number of the properties and conditions of a heart assist system or of patients that are important for the user from a technical and from a clinical aspect cannot be detected and processed due to the available technology. This is caused, on the one hand, by the sensor technology used in the heart assist systems and also by the frequently hardly available construction space that requires an even frequently multiple use of various sensors for specific measurement variables and at different points within a heart assist system. Furthermore technical flow compromises or compromises with respect to hemocompatible blood management frequently have to be accepted since, for example, the welding of a flat membrane as a mount for the sensors is required (e.g. restriction of the technical flow design, activation by roughnesses of a weld seam/gap/step etc.) or the geometrical properties of the blood conducting path for the usability of the respective measurement apparatus has to be correspondingly adapted (e.g. flattening of the inner wall, large-area thinning out of a tube wall or tangential chamber, straightening a blood conducting wall to create construction space).

In addition, any sensor system in the inlet region or outlet region of a blood pump has to be electrically connected to the overall system. This also includes the electrical contacting of individual physical sensors or the connection of entire assemblies. Due to tight space conditions between the inner wall and the outer wall of the blood pump, the sensor elements and also the wiring have to have a small construction height.

The object of the present invention is to provide a component for conducting a fluid having a sensor, for example for a heart assist system, that solves the above-described problem and wherein the sensor is integrated in the component such that important conditions of a fluid system connectable to the component, for example of a heart assist system, and also of a patient interacting with the heart assist system, can be detected, the dimensions of the component are not increased, the sensor does not influence the fluid or the fluid flow and does not come into contact with an installation environment of the component.

The component in accordance with the invention for conducting a fluid having a sensor comprises an inner and an outer wall, wherein the inner wall is configured to conduct the fluid, the outer wall terminates the component to the outside, and a wall region is formed between the inner and outer walls. The component in accordance with the invention is characterized in that the sensor has an electromechanical sensor element and is arranged in the wall region at the inner wall, wherein the sensor is adapted to measure a degree of deformation of the inner wall in the region of the sensor by means of the sensor element and to output it as an electrical signal, wherein the electromechanical sensor element preferably has a length and/or preferably has a width of ≤50 µm.

A sensor is here understood in some embodiments as a layer design that preferably has two electrical contacts in a first layer that are separated from one another by a gap. The sensor element can then be arranged on the electrical contacts in a second layer. The sensor element is an electromechanical element, preferably a nanostructural expansion element, and does not itself have any further components such as electrical conductors. The sensor element preferably extends in a transverse direction over the gap. The sensor element can furthermore project into the first layer in the region of the gap. The sensor furthermore preferably comprises two bond pads, with a respective bond pad being electrically contacted by one of the electrical contacts.

The inner wall does not have any sensor induced material transitions, steps, or gaps (such as weld seams or similar) on the fluid conducting side even after an embedding of the sensor.

The invention described here can be used for all implantable and hemocompatible materials and is able to measure the smallest deflections (strokes, vibrations, impulses) without any invasive effects on a blood conducting element that cannot be detected using conventional sensors (e.g. DMS, ultrasound sensors, optical sensors) and can output this information. The same applies to the same degree to the required construction space since the sensor used itself only takes up a few cubic micrometers, can thus be integrated very easily, and can be applied in part to previously inaccessible structures.

In an advantageous embodiment of the invention, the sensor element can be a nanostructural expansion element that is applied materially integral to the contacts so that the contacts electrically contact one another via the sensor element, with the electrical contacts being applied to the inner wall such that the sensor element deforms with the inner wall on a deformation of the inner wall in the region of the sensor so that the electrical signal is measurable between the electrical contacts. The deformation of the inner wall can be detected, for example, as a surface expansion or as a raising of the wall region.

In a further embodiment, the sensor can have at least one meandering measurement structure, advantageously a plurality thereof, that are connected together to form a measurement bridge. The at least one meandering measurement structure is arranged in a direction transversely to the axial direction, i.e. transversely to the direction of the flowing fluid, such that the individual sections of the meander substantially extend in parallel with the transverse direction and thus a surface expansion of the thinned or thinned out wall regions can be detected. For special applications, the meander structure can also be arranged in parallel with the flow direction. The meandering measurement structure can, for example, be manufactured as a metal structure such as a gold structure a silver structure, or similar applied materially integral to an insulating substrate. The insulating substrate and the sensor element can, for example, be applied directly to the thinned out wall region, e.g. by means of physical or chemical deposition processes or similar processes known in microelectronics for the application of conductive or insulating structures.

In other embodiments, a raising of the thinned out wall region in a radial direction can additionally or alternatively be measured on the basis of a pressure or pressure difference prevailing in the fluid conducting section of the component. The raising of the thinned out wall regions can, for example, be detected by means of an optical sensor, a resistive sensor, or a capacitive sensor.

The expansion or raising can also be used to determine a parameter of the fluid flowing through, for example to detect a pressure of the fluid flowing through, both in the case of a measurement of the surface expansion or of a measurement of a raising of the thinned out wall region. If a plurality of these sensors are used at different points or locations of the component, a pressure difference of the fluid flowing through can also accordingly be determined.

A plurality of sensors can furthermore be arranged in the wall region at the inner wall. Four sensors can in particular be arranged at the inner wall that are preferably connected to one another to form a full bridge or half-bridge circuit to reduce a temperature dependence of the sensors.

An electrical insulation layer that is connected to the inner wall and to the electrical contacts materially integral can furthermore be arranged between the inner wall and the electrical contacts of the sensor.

The sensor element can in particular have a nanocrystalline composite material (nanocomposite) that can preferably be printed by means of nano 3D printing and whose composition can be modified as desired. The sensor element can furthermore comprise metal and/or a semiconductor material. The sensor element can also comprise a metal doped with charge carriers and/or a semiconductor material doped with charge carriers to set an electrical conductivity and/or an electrical resistance of the sensor element.

The electrical signal can in particular include a change of an electrical resistance of the sensor.

It is advantageous if the sensor element has a length and/or a width of ≤15 μm, in particular ≤10 μm, in particular ≤3 μm and/or a thickness of ≤50 μm, in particular ≤15 μm, in particular ≤10 μm, in particular ≤3 μm.

The electrical contacts can preferably be applied to the inner wall such that there is a gap between the contacts of ≤50 μm, in particular ≤30 μm, in particular ≤15 μm, in particular ≤10 μm, in particular ≤3 μm, with the gap being completely covered by the sensor element in a transverse direction.

It is furthermore preferred if the sensor is arranged in a thinned region of the inner wall. A wall thickness in the thinned region is preferably ≥5 μm, in particular ≥100 μm and/or ≤500 μm, in particular ≤200 μm, preferably between 15 μm and 50 μm.

The wall region of the inner wall in whose region the sensor is arranged is preferably a thinned out wall region. In some embodiments, the inner wall is produced in one piece, for example as a tubular section. The thinned out wall region can here be produced by material removal from the non-fluid conducting side, for example by milling, erosion, or by grinding post-machining. The thinned out wall region of the inner wall can also be understood as a membrane having a varying wall thickness. The wall thickness of the membrane can here be between 10 μm and 200 μm, preferably between 20 μm and 100 μm. Depending on the material removal, the surface usable as a membrane for the sensor, i.e. that surface in which a surface expansion and/or a raising of the membrane in a radial, outwardly directed direction is measurable by means of sensors, an axial expansion of 2 mm to 1 cm, preferably of 2 mm to 7 mm and a transverse expansion extending transversely to the axial direction (i.e. transversely to a flow direction of the fluid) of 0.5 mm to 3 mm, preferably 0.5 mm to 1.5 mm. I.e. the wall thickness in this surface is reduced such that the surface expansion or raising can be detected in the required measuring accuracy with the sensor described here; for example, a pressure difference of up to 0.1 mbar can be detected.

From a wall thickness of the membrane of more than 250 μm onward, a surface expansion is practically no longer measurable so that regions of the inner wall having more than 250 μm cannot be called a thinned out wall region in the sense of this application. However, in embodiments in which the raising of the thinned out wall region is detected, the wall thickness can be somewhat higher than the above-designated 250 μm.

In some embodiments, the thinned out wall region has a variable wall thickness, i.e. the wall thickness can become thinner in the direction transversely to the axial direction of the component from a region of the inner wall having a substantially unchanging wall thickness toward a point of minimal wall thickness. The reduction of the wall thickness can here, for example, progress continuously toward the minimum. In other embodiments, a reduction of the wall thickness can take place by means of grooves that should provide a better regional surface expansion. The grooves can furthermore also be combined with the otherwise continuous reduction of the wall thickness.

In the embodiments in which the membrane has grooves, three grooves can be used, for example. In this respect, two grooves flank a middle groove, with the smallest wall thickness being present within the middle groove. In this arrangement, a particularly easily measurable surface expansion can be set in the region of the middle groove. The wall thickness of the two outer grooves can he be considerably higher than the wall thickness of the middle groove. While the middle groove can, for example, have a wall thickness between 20 µm and 50 µm. the outer grooves can have a remaining wall thickness of 50 µm to 200 µm, preferably less than 100 µm. The expansion of the outer grooves in the transverse direction can amount to between 200 µm and 2000 µm; the expansion in of the middle groove in the transverse direction can amount to between 50 µm and 200 µm. The outer grooves are preferably arranged in parallel with and/or at the same distance from the middle groove in the transverse direction.

The component can in particular be a blood pump, with one or more sensors being arranged in the inlet region and/or in the outlet region in the wall region at the inner wall of the blood pump, and a blood pressure in the inlet region and/or outlet region, an instantaneous flow amount, and/or running properties of the blood pump can be determined from the deformation of the inner wall.

The component can furthermore be a blood pump having a movable conveying element, with one or more sensors being arranged at the inner wall in the wall region of the blood pump, and with an abutment of the conveying element at the inner wall being able to be determined from the deformation of the inner wall.

The component can furthermore be a mechanically supported rotary blood pump, with one or more sensors being arranged in the region of the bearing mount in the wall region at the inner wall and with a bearing force and/or a bearing wear being able to be determined from the deformation of the inner wall.

A plurality of sensors can furthermore be arranged along a periphery of the inner wall in the wall region or in the region of the inner wall of similar static pressure conditions. Mean values of the measured values can be formed with the aid of the plurality of sensors and measurements of the sensors can thus be designed as more accurate and independently of local flow structures.

In accordance with a further aspect of the invention, electrical connection elements can be arranged in the wall region via which the sensor is connected to a processing device.

The connection elements can in particular comprise a printed circuit board, with one or more sensors being directly connected to the printed circuit board via the electrical contacts or via bond wires or individually insulated leads, in particular Teflon insulated leads.

Electrical components can furthermore be arranged on the printed circuit board for the pre-processing of the electrical signals, in particular for preamplification.

The present invention also includes a method of manufacturing a component for conducting a fluid having a sensor. The method in accordance with the invention comprises the following steps: forming an inner and outer wall of the component, with the inner wall being configured for conducting the fluid and the outer wall being configured to terminate the component to the outside, and the inner wall and the outer wall being able to be joined together such that a wall region is produced between the inner and outer walls; arranging a sensor having an electromechanical sensor element in the wall region at the inner wall, with the sensor being adapted to measure a degree of deformation of the inner wall in the region of the sensor by means of the sensor element and to output it as an electrical signal, with the electromechanical sensor element having a length and/or a width of ≤50 µm; and joining the inner and outer walls together.

In a further advantageous embodiment of the method in accordance with the invention, an insulation layer can be applied to the inner wall in the wall region before the arrangement of the sensor. This is in particular necessary when the inner wall comprises an electrically conductive material to reduce a short circuit between the contacts.

The arrangement of the sensor can in particular comprise the following steps: applying electrical contacts to the inner wall or to the insulation layer to pick up the electrical signal and applying an electromechanical sensor element to the electrical contacts.

The method can in particular comprise a wall thickness of the wall being thinned in the region of the sensor before the arrangement of the sensor at the inner wall or before the application of the insulation layer, in particular being thinned to a wall thickness of ≥5 µm, in particular ≥100 µm and/or ≤500 µm, in particular ≤200 µm.

The method can furthermore comprise the sensor element being applied to the insulation layer by means of nano 3D printing, sputtering, or by means of an etching process.

The method can furthermore comprise a sensitivity of the sensor element being set by introducing a higher or lower number of charge carriers into the sensor element.

Different embodiments of a component in accordance with the invention will be described in more detail in the following with reference to Figures. Different elements that are essential to the invention or are also advantageous and that go further are named here within the framework of a specific example, with individual ones of these elements also being able to be used as such to further develop the invention—also removed from the context of the respective example and further features of the respective example. Moreover, identical or similar reference numerals are used for identical or similar elements in the figures, and the explanation thereof is therefore partially omitted.

The following embodiments primarily relate to the field of blood conducting components such as blood pumps for heart assist systems. The invention is, however, not restricted to this field, but is rather applicable to fluid conducting components of any kind.

It is an aim of the present invention with respect to blood conducting components to measure the smallest deflections (strokes, vibrations, impulses) without invasive effects on a blood conducting element and to output this information. For this purpose, specific measurement configurations can be provided that enable the measurement of signals without a negative influence on technical flow performance and on hemocompatible performance of a blood conducting and/or blood conveying system.

This aim is achieved in that one or more nanostructures or microstructures (sensor element) are applied at a corresponding distance and extent to a hemocompatible or coated material (component). Since these nanostructures serve as conductor tracks, they consist of a conductive material that can be applied with the aid of technical microsystem production methods (e.g. lithographically, microetching, PEVDM etc.). A further requirement is the electronically passive application surface on which the sensor element is applied, which in the case of a conductive inner wall additionally requires an insulation layer. A nanostructural expansion element is then applied between two conductor tracks (electrical contacts) that result in a changed conductivity in the expansion element with the smallest deflections due to the length change of the expansion element resulting therefrom and thus makes a voltage delta between the conductor tracks measurable.

FIG. 1a) shows a schematic plan view (not to scale) of a part of a single sensor. Two areally formed electrical contacts 1 can be seen that are arranged next to one another such that a gap 3 of approximately ≤50 μm is formed between the contacts 1. The gap 3 is covered in a transverse direction by a nanostructural expansion element 2 as a sensor element. Two bond pads of the sensor are not shown here with a respective one contact surface 1 being contacted by a respective one bond pad to connect the sensor to a processing device.

FIGS. 1 b)-f) show an arrangement of a sensor for different examples of an inner wall having different geometries. The design of the direct application surface of the inner wall on which the sensor is arranged plays a subordinate role here since only a sufficient deflection is required that can be in the nanometer range to subnanometer range. A plurality of measurement techniques or also FEM simulations can be appropriate for a quantification of the deflection to be expected. Free form surfaces are also possible as application surfaces. FIG. 1 b) shows a cross-section through a planar inner wall 4 in a sensor region. The inner wall 3 is formed as planar both on a wall region side 6 and on a fluid region side 7. An insulation layer 5 is applied to the inner wall 4 in the wall region. The electrical contact surfaces 1 are applied to the insulation layer 5 while forming a gap 5. The sensor element 2 bridging the gap 3 is arranged on the contact surfaces 1. FIG. 1 c) shows a cross-section through a sensor region of an inner wall 4. The inner wall 4 is formed as planar on the wall region side 6 and the inner wall 4 is formed as concave on a fluid region side 7. The sensor is arranged at a point of minimal wall thickness of the inner wall to optimize the sensor signal. FIG. 1 d) shows a cross-section through a sensor region of an inner wall 4 that is curved overall so that its wall thickness is constant. FIG. 1 e) shows a cross-section through a sensor region of an inner wall 4, with the wall region side 6 having a complicated geometry and the application surface of the sensor representing a free form surface. The fluid region side 7 is formed as concave and the sensor is advantageously arranged at a point of minimal wall thickness of the inner wall 4 to optimize the sensor signal. A sensor application in a region of the inner wall 4 is equally possible in which both the wall region side 6 and the fluid region side 7 have complicated geometries and free form surfaces. FIG. 1 f) shows a cross-section through a sensor region of an inner wall 4, with the inner wall being thinned in the sensor region, for example, by means of milling, boring, or by means of a chemical process. With a non-conductive inner wall, an insulation layer can be dispensed with. As can be seen from FIGS. 1 c)-f), the inner wall 4 does not have any sensor induced material transitions, steps, or gaps (such as weld seams or similar) on the fluid conducting side 7 even after an embedding of the sensor.

The following integration options for sensors within a blood conveying or blood conducting system are possible:

1. Pressure Measurement in a Blood Pump Tube

Figure 2:
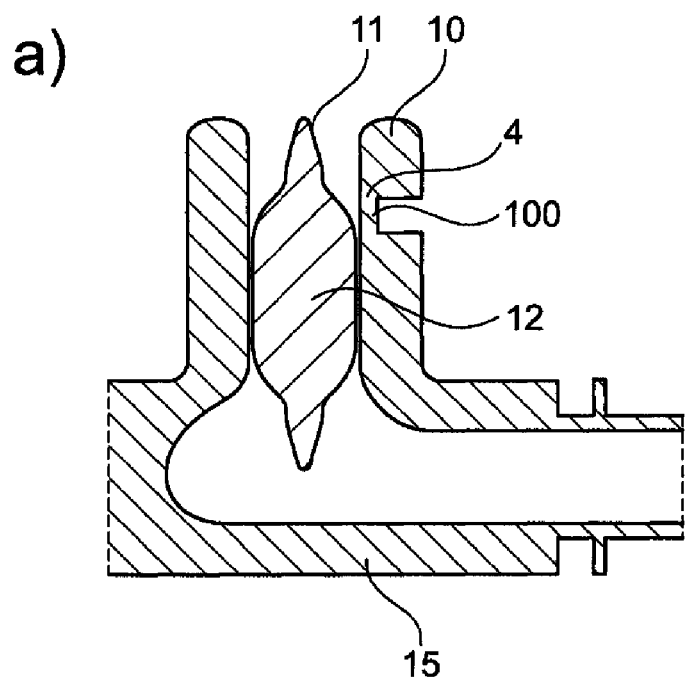
FIG. 2 different variants of a blood pump tube with sensors.
Figure 2:
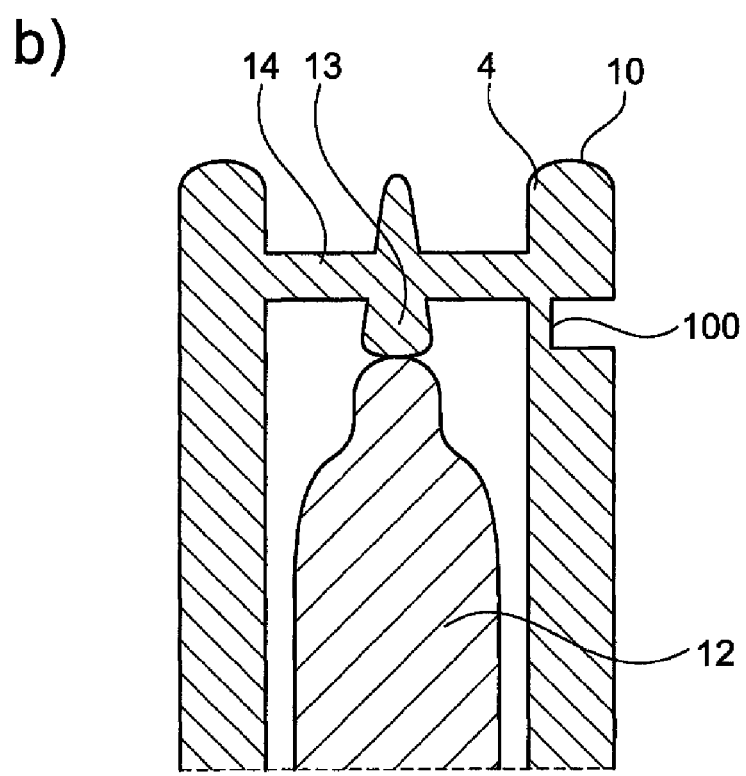
Figure 3A:
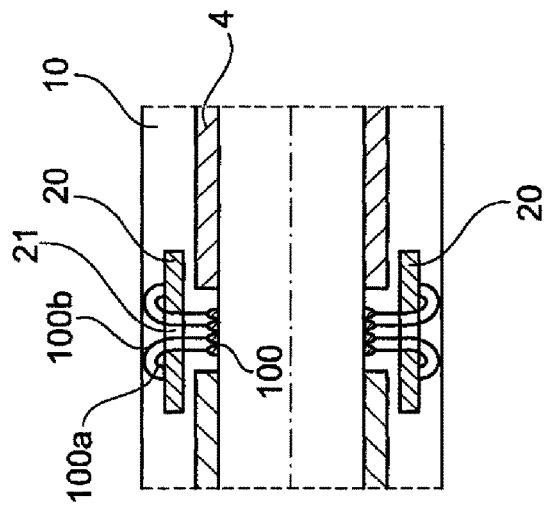
Figure 3A:
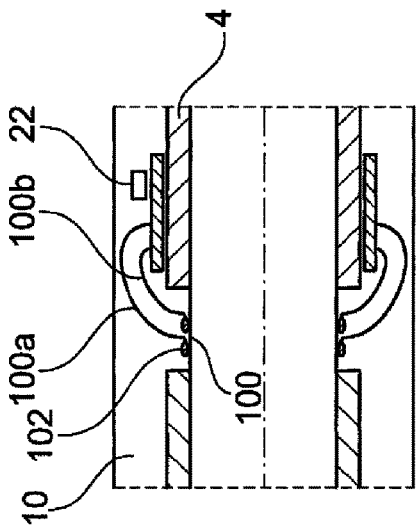
Figure 3B:
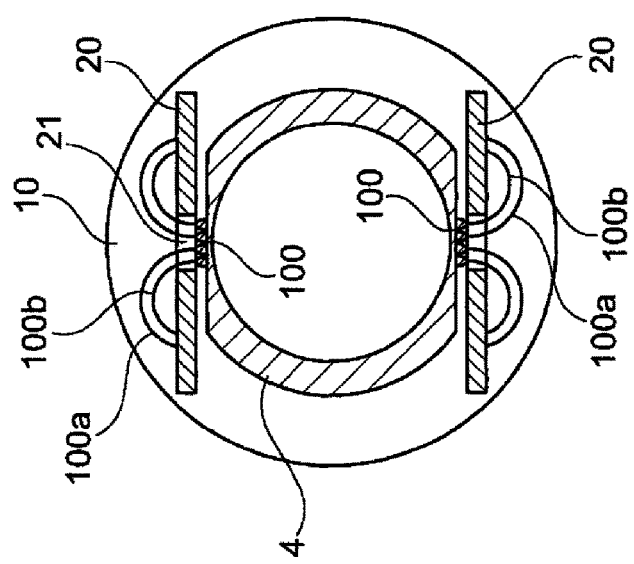
Figure 3B:
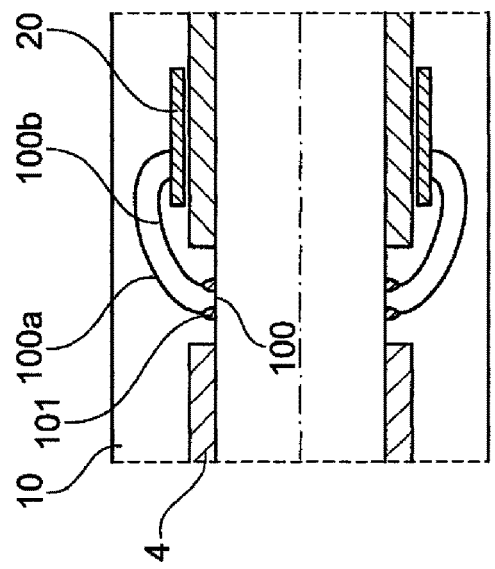
Figure 3E:
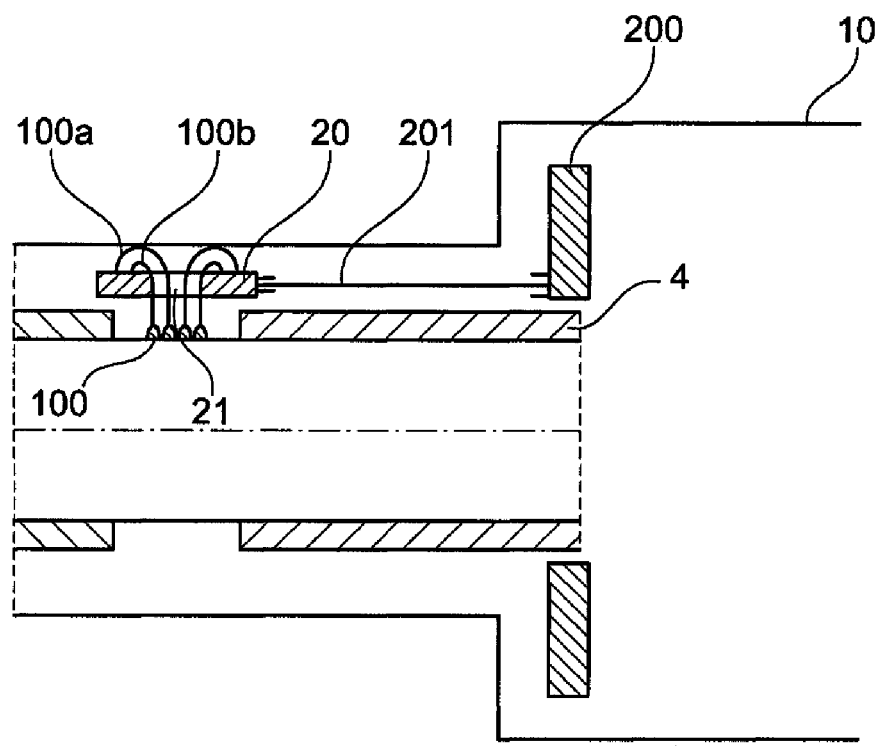
Figure 3F:
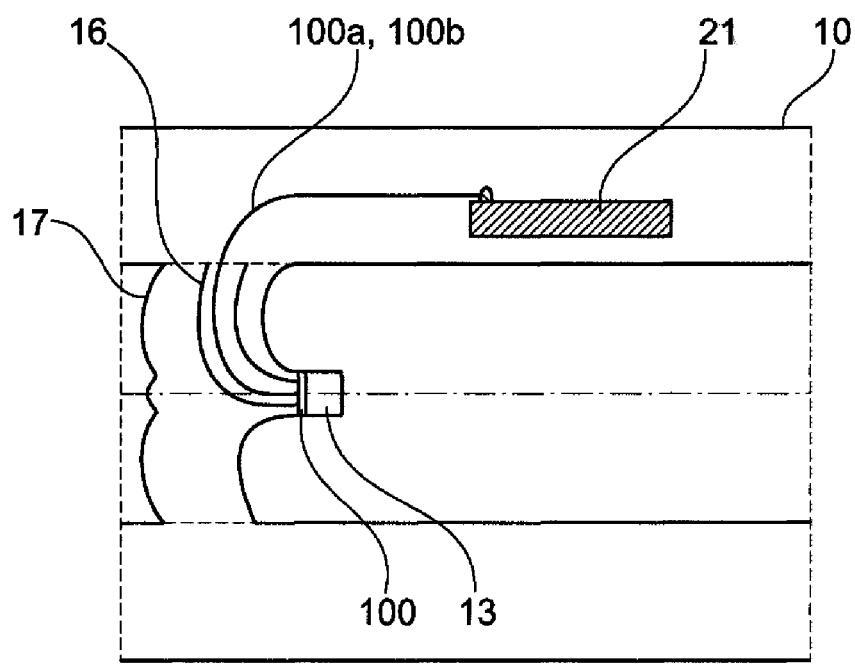
Figure 3G:
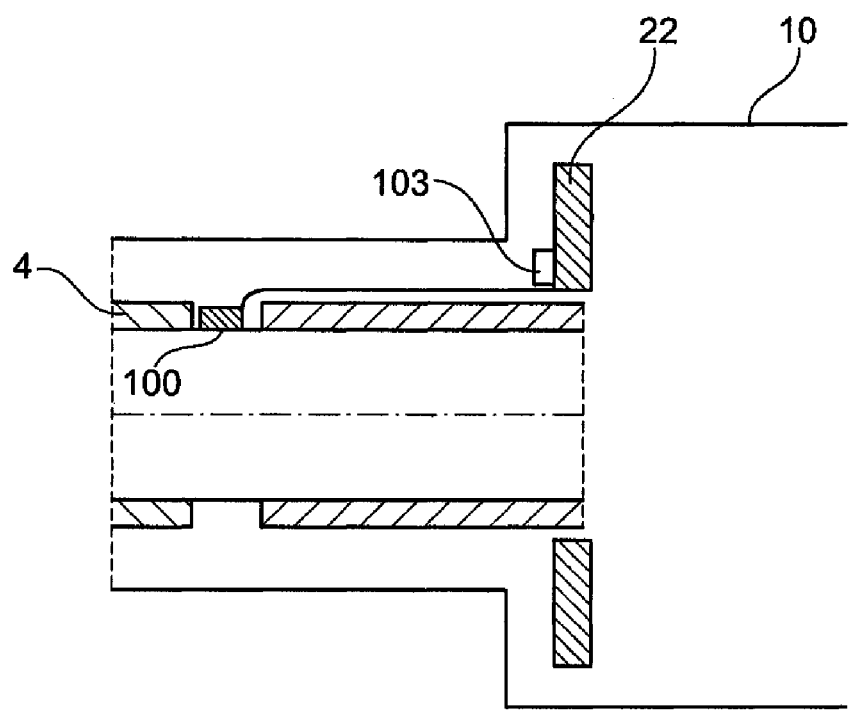

FIG. 2 a) shows an inner wall 4 of a blood pump tube 10 having an axial flow blood pump 11 arranged therein. One or more sensors 100 are applied in a configuration described in FIGS. 1 c)-f) to a thinned point of the inner wall 4 in the inlet region (optionally also in the region of the outlet cannula/diffuser) of the blood pump tube 10 to measure a blood pressure in a ventricle connected to the blood pump tube 10. The measured deflection allows a conclusion on the ventricle pressure if the normal pressure or e.g. the pressure within the hermetically sealed blood pump tube 10 is available as a reference. The pressure within the hermetically sealed blood pump tube 10 can be determined with the aid of a reference pressure sensor (e.g. an absolute pressure sensor) arranged in the blood pump tube 10.

2. Flow Measurement

One or more sensors 100 are applied in a configuration described in FIGS. 1 c)-f) in the inlet and outlet regions of a blood pump tube 10 to determine the instantaneous flow amount in a blood pump. The instantaneous blood flow can be determined with the aid of a HQ characteristic curve of the respective heart assist system since the ventricle pressure (Application 1.) is known.

3. Abutment Detection

One or more sensors 100 are applied as in FIGS. 1 c)-f) and FIGS. 2 a) and/or b) to recognize an abutment event in a heart assist system that has a rotor 12 or a movable element for conveying/conducting blood. In FIG. 2 b), the sensor 100 is arranged close to a bearing mount 13 for the rotor 12. Alternatively or additionally to the application options for the sensors 100 shown in FIGS. 2 a) and b), a plurality of sensors 100 can also be arranged distributed evenly over the total inner wall 4 of the blood pump tube 10, embedded in an inlet and/or outlet cannula (silicone cannula, plastic tube, metal tube) and/or in a connector at the inlet/outlet (metal, plastic). A conclusion on an unwanted abutment situation can be drawn from the deflection impulses at the sensor surface or surfaces occurring during the event and corresponding measures or signaling can be initiated.

4. Measuring the Bearing Forces

A rotor 12 within a mechanically supported heart assist system generates an axial force on the conveying of blood in dependence on the instantaneous counter-pressure, said axial force being taken up in a mechanical bearing 13. One or more sensors 100 are applied in the configuration shown in FIG. 2 b) to determine the bearing force. The bearing mount 13 located in the inlet is designed here such that the bearing force (axial force of the rotor 12) taken up results in a deflection that is measured either directly at a strut 14 or a blood tube wall 4. The instantaneous blood flow can be determined with the aid of the HQ characteristic curve of the respective heart assist system since the ventricle pressure (Application 1) is known.

5. Wear at Mechanical Bearings

A rotor 12 within a mechanically supported heart assist system generates an axial force on the conveying that acts taken up in a mechanical bearing 13. If this rotor 12 is installed with a specific preload required as known (is typically required to avoid gap formation between the bearing surfaces), a deflection in the bearing 13 is to be measured (Application 4). If the axial expansion of the rotor 12 is reduced due to wear in the bearing 13, the deflection at the bearing point 13 produced by the preload also thereby falls. The wear at a bearing 13 can thus be detected by the high resolution measurement of the sensors 100 and corresponding measures are initiated if a hazardous situation is present.

6. Material Fatigue

The interference variables described in Application 5 equally allow a conclusion of material fatigue at the bearing 13.

7. Vibration Recognition

Since the sensors 100 detect the smallest deflections, they are also suitable for monitoring the running properties of a heart assist system (measurement of periodic vibrations). Unwanted vibrations or sporadic impulses that occur e.g.

when a patient falls or due to a long delay on e.g. an accident can therefore be recognized and correspondingly processed.

8. Recognition/Distinction of Sporadic Interference Variables and Systematic Interference Variables Logical processing of the signals measured in Application 7.

9. Thrombi Detection

With a thrombi passage in a blood pump, different scenarios are conceivable that result in a mechanical vibration/impulse. Such an event could therefore be recognized with a vibration sensitive blood pump and can be used to initiate corresponding measures.

An electrical connection to a processing device is necessary to operate the sensor 100 in the blood pump tube 10 or in the outlet chamber/outlet tube 15. The electrical connection can take place via electrical connection elements arranged between the outer wall and the inner wall. Implantable rotary blood pumps generally comprise an inner pump tube as an inner wall whose inner surface conducts the blood. The motor or other electronic or electromechanical assemblies, e.g. sensors, active magnetic bearing components, are accommodated outside the inner pump tube in almost all blood pumps. Parts of these sensors can also be implemented as non-encapsulated sensors. An outer pump tube or a housing as an outer wall is likewise welded on in almost all rotary blood pumps for the hermetic covering of these components. The electrical connection elements are located within the hollow space (wall region) between the inner and outer pump tube or housing.

Connection structures are shown in FIGS. 3 *a*)-*g*) that make it possible to electrically connect the sensors 100. It should also be possible to respectively connect more than one sensor 100. The number is meaningfully between one and four sensors. The electrical connection and signal pre-processing device are additionally shown.

FIG. 3 *a*) shows a cross-section at the left and a longitudinal section through a pump tube 10 at the right. A printed circuit board (PCB) or MID receives the two bond wires 100*a* and 100*b* of one respective sensor 100 that is positioned on the inner tube 4 of the pump tube 10. The bond wires 100*a*, 100*b* are applied as a ball by means of wire bonding and are rewired on the printed circuit board 20. The (flexible) printed circuit board 20 is directly above the sensor 100 and has a hole or a via 21 for the bond wires 100*a*, 100*b*.

FIG. 3 *b*) shows a printed circuit board (PCB) or MID 20 next to the sensor 100. The bond wires are applied as a ball 101 (left) or wedge 102 (right) to the sensor 100 and are rewired on the circuit board. Passive or active electrical components 22 can additionally already be accommodated on the printed circuit board 20 as a pre-processing device to carry out a first filtering or pre-processing.

FIG. 3 *c*) shows a 3D MID printed circuit board 20 as a connector board. It does not require any bond wires for the connection and can be soldered or plugged directly onto the sensor 100. Electrical components 22 can also already be provided here as a pre-processing device.

FIG. 3 *d*) shows a complete sensor assembly 100 that is electrically connected either to a plugged on and soldered circuit board 20 or via individually insulated wires 23. The insulation 24 can, for example, take place via a Teflon jacket that has extremely high electric strength with a very small thickness.

In FIG. 3 *e*), the electrical connection of a rewiring circuit board 20 at the sensor 100 to form a main circuit board or further pump electronics 200 in the pump tube 10 is shown. This connection is established by plugged or soldered galvanic conductors 201 and communicates the sensor data to the pump electronics 200 for further processing. The forwarding can also be carried out via 3D formed circuit boards (e.g. MID circuit boards). A further possibility of transferring data within the pump tube 10 is a wireless communication interface.

In FIG. 3 *f*), the pump tube 10 has a bearing stator 13 that is disposed in the flow. A sensor 100 in this bearing stator 13 is electrically connected within the stator structure 17 via a passage 16. For this purpose, leads 100*a*, 100*b* are placed through the passage 16 from the sensor 100 up to the evaluation or processing electronics 21. In the simplest case, the passage 16 is a bore through the stator blades 17 that are connected to the pump tube 10.

In FIG. 3 *g*), a reference pressure sensor 103 can be attached within the pump tube 10 in addition to the actual pressure sensitive sensor 100. This sensor 103 is in the simplest case an IC on an electronic circuit board 22 within the pump housing. Fluctuations of the reference pressure in the hermetically sealed pump housing can be detected by means of this pressure sensor 103. The pressure fluctuations can be used to compensate measurement errors of the actual sensor 100.

Figure 4:
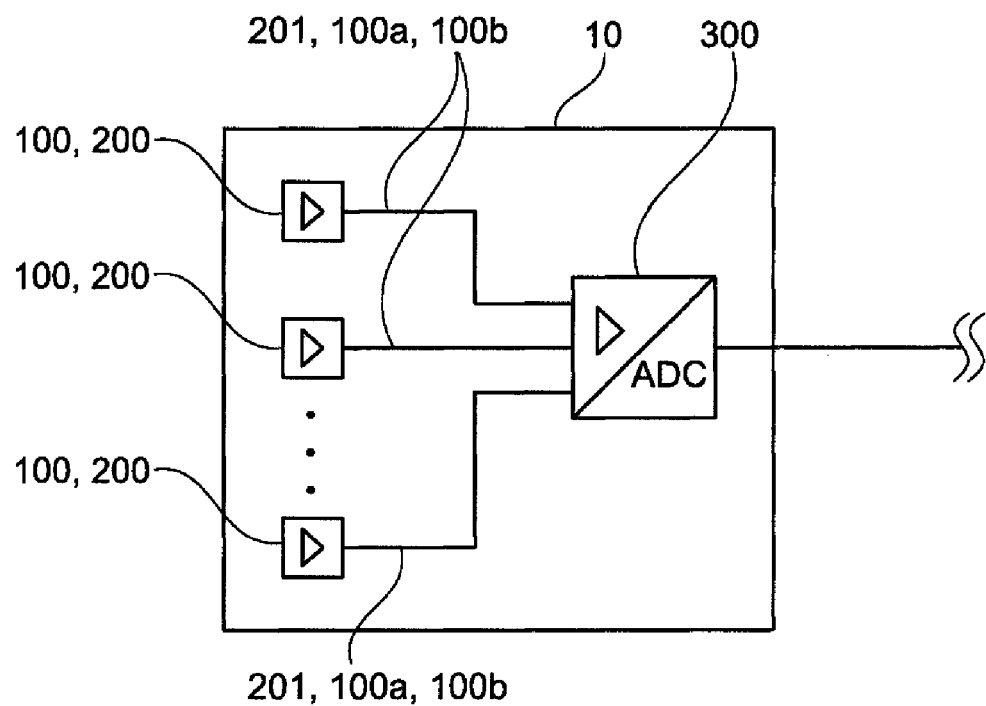
FIG. 4 a simplified representation of the connection of the sensors to a processing device.
Figure 5C:
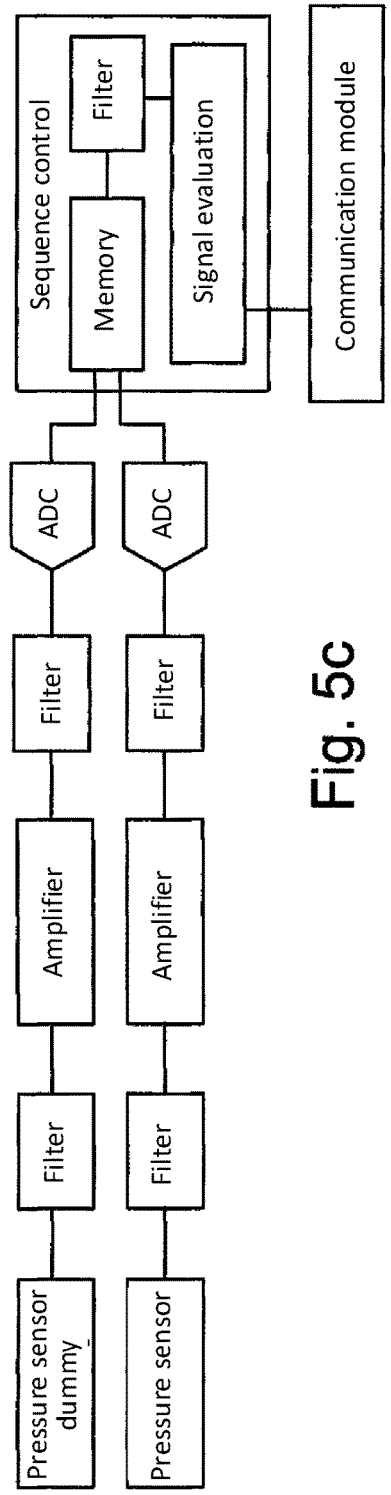
Figure 5D:
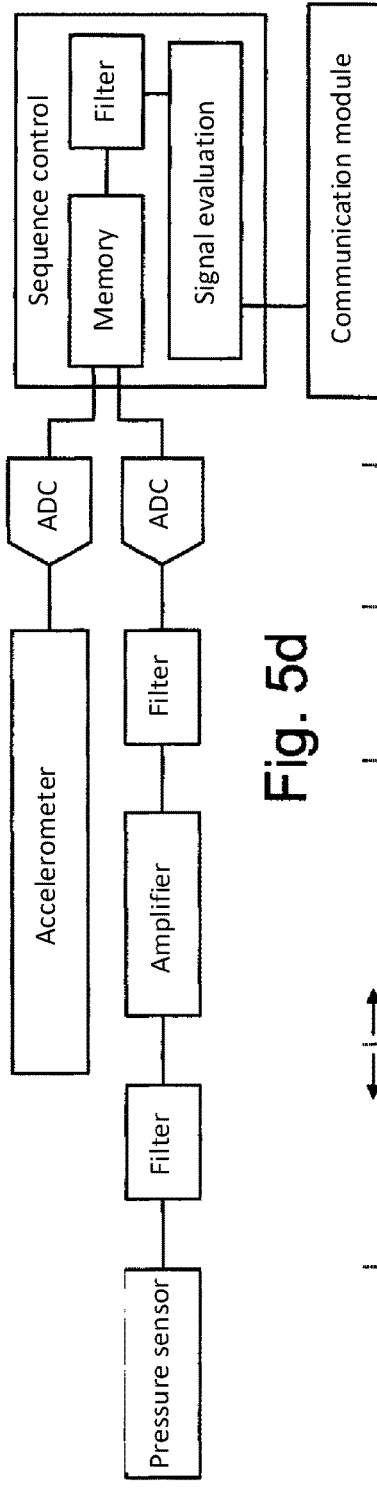
Figure 5E:
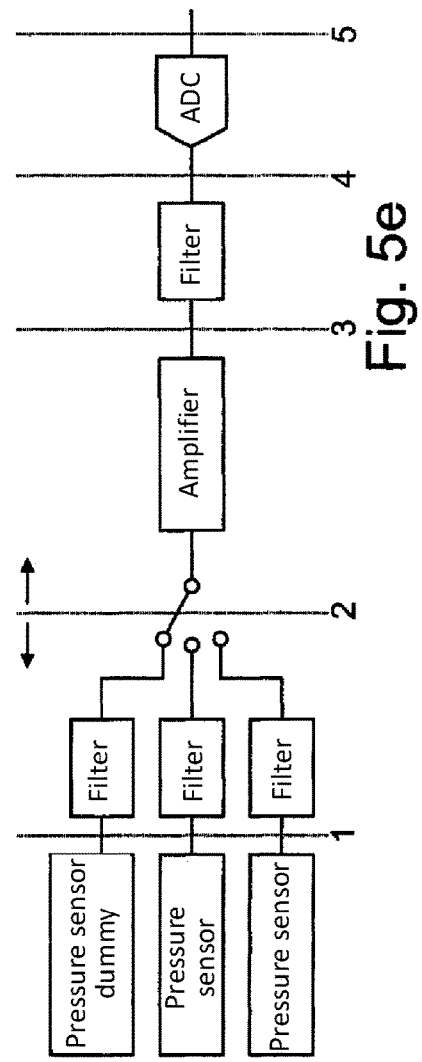
Figure 5F:
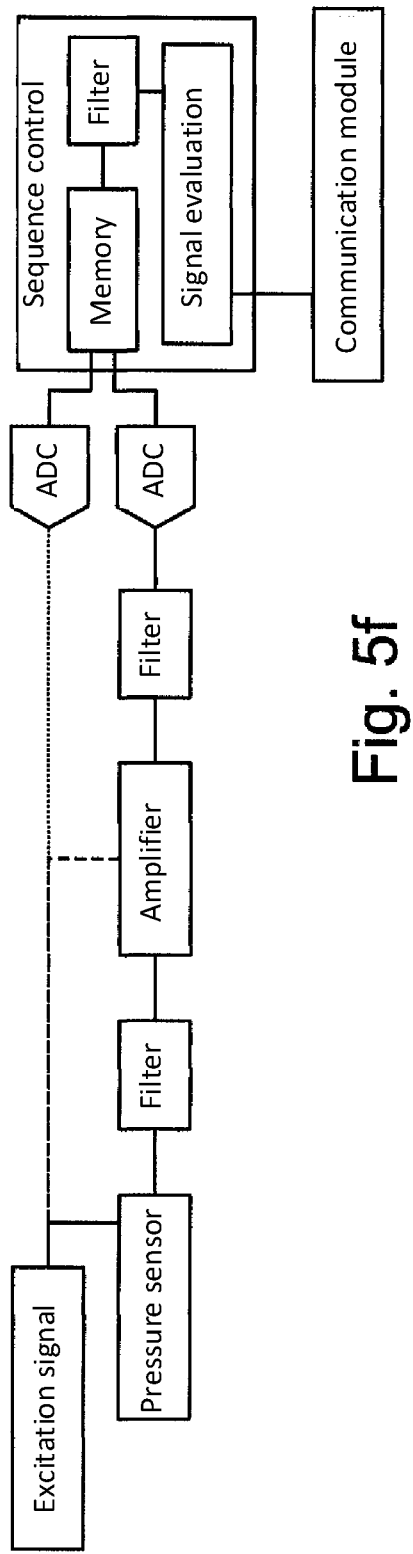

FIG. 4 shows a simplified representation of the connection of the sensors 100 to a processing device. The signals of individual sensors 100 can be combined and processed on pump electronics 300 within the pump tube 10 via the electrical connections 100*a*, 100*b*, 201. In this process, the rewiring circuit boards 300 can be purely passive or can already include a pre-processing.

The signal of the pressure sensor can be amplified and filtered for the signal acquisition. The filters can each be applied in front of and/or behind the amplifier. The amplifier can also be designed as an active filter element. The amplified signal can be digitized by an analog-to-digital converter (ADC). The signal curve can be stored and further filtered as required after the digitizing. A digital filtering takes up no space in the pump in comparison with a discrete filtering.

The filters should remove interference from the useful signal. Interference can have its origin outside the pump such as EMC or vibrations. Interference that originates from the pump itself is, for example, the magnetic stray field of the magnet in the pump rotor. Interference such as EMC can be filtered via a frequency selection. If more is known about the interference signal, the interference can be filtered via a correlation filter. The correlation filter can be carried out in the sequence control or as an active filter element. The interference influences can also be acquired via a dummy pressure sensor. The dummy pressure sensor should be set up exactly as the pressure sensor, with the difference that it has a different pressure dependence than the pressure sensor. The sensitivity to interference should be comparable. The interference influences can be canceled by a comparison of the dummy pressure sensor signal and the pressure sensor signal. The situation is comparable with the interference from the stray field of the pump rotor magnet. Since the position and speed of the rotor magnet is known to the motor driver, this signal can likewise be removed by calculation.

A further form of interference arises on vibration or acceleration of the pump. This interference influence can be measured by an accelerometer, a dummy pressure sensor, or a differential pressure sensor pair and can subsequently be filtered. If a plurality of pressure sensors is accommodated, common elements of the signal chain can be connected to the different sensors by means of a multiplexer. The position of the multiplexer is variable in this context and can, for example, be after the first filter.

FIG. 5 *a*) shows a signal chain that starts from the pressure sensor comprising a pressure transducer, filter, amplifier, ADC, sequence control with memory, and a communication module. The filters can be respectively omitted or can be combined with adjacent modules, for example the amplifier.

FIG. 5 *b*) shows a signal chain starting from the pressure sensor including scanning and filtering the interference influences.

FIG. 5 *c*) shows a signal chain starting from the pressure sensor with the pressure sensor dummy for interference suppression.

FIG. 5 *d*) shows a signal chain with a pressure sensor and accelerometer for suppressing shock and vibration.

In FIG. 5 *e*), the number of components can be reduced by the use of a multiplexer. The multiplexer can be positioned at positions 1 to 5.

FIG. 5 *f*) shows an excitation of the pressure sensor by an excitation signal. The excitation signal can be additionally connected to the amplifier or to the sequence control. This enables a very selective frequency or correlation filtering.

Figure 6:
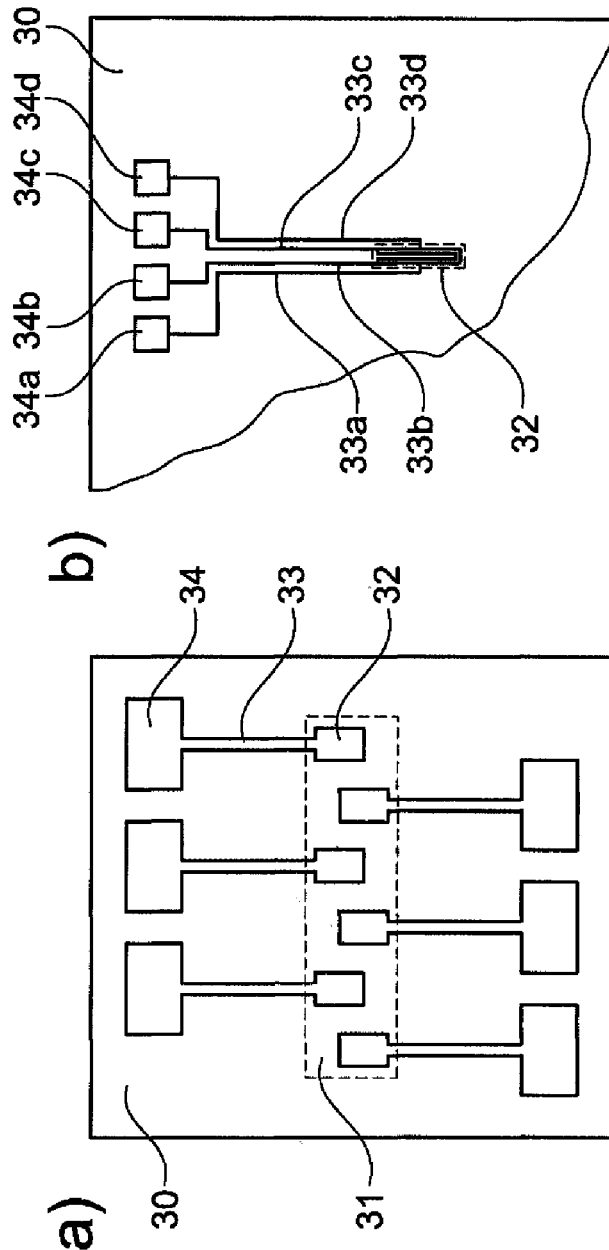
FIGS. 6a and 6b a plan view of a sensor region having six sensor structures, and a schematic representation of a sensor structure comprising four sensors connected for form a full bridge.

Bridge circuits, in particular composed of four sensors, are typically used for the temperature compensation of the sensors. This is, however, only necessary when the interfering influences negatively influence the resolution or the desired long term stability. Half-bridge circuits and full bridge circuits are in particular used. FIG. 6*a*) shows a plan view of a sensor region 30 having six sensor structures 32, 33, 34. FIG. 6*b*) shows a schematic representation of a sensor structure 32, 33, 34 comprising four sensors connected to form a full bridge. The sensors of the sensor structures 32 33, 34 are arranged in a region 31 of maximum deformation within the sensor region 30. Four sensors are connected together to form a full bridge circuit 32 (measurement bridge) for the temperature compensation of the sensors in each sensor structure 32, 33, 34. Each full bridge 32 has four or six bond pads for the electrical connection to a processing device.

Figure 7A:
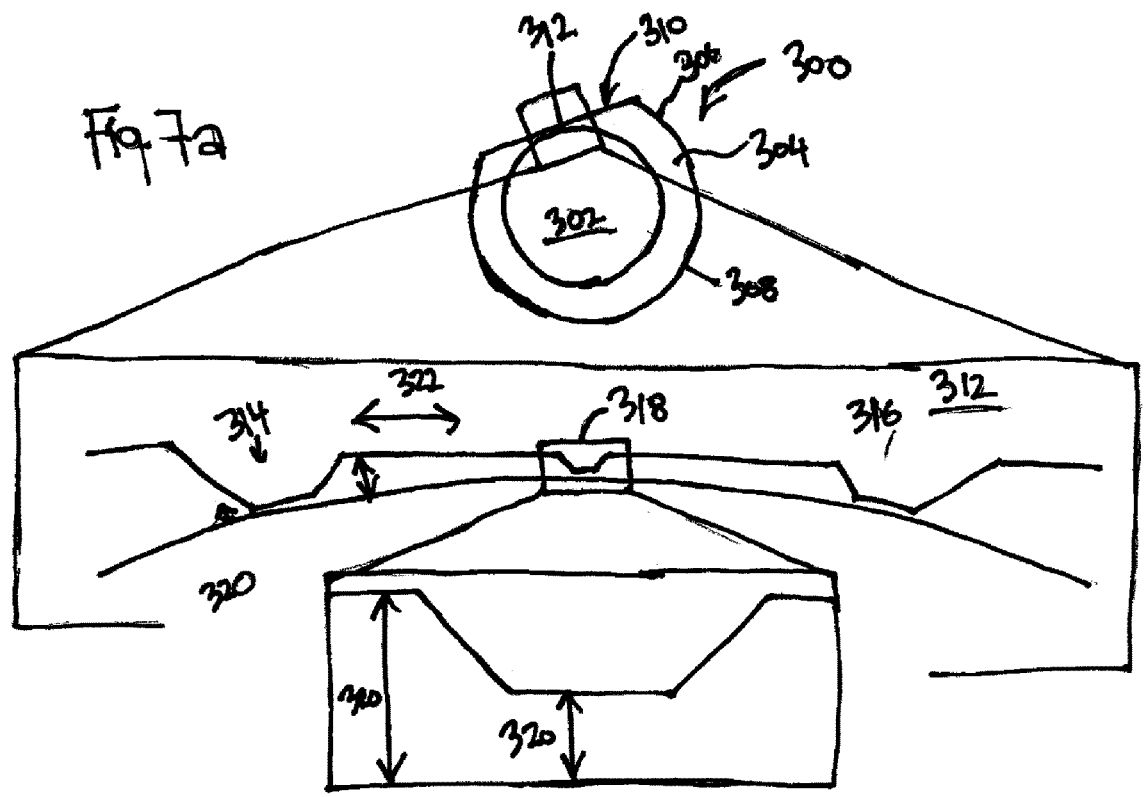
FIGS. 7a and 7b cross-section through an exemplary thinned out wall region.
Figure 7B:
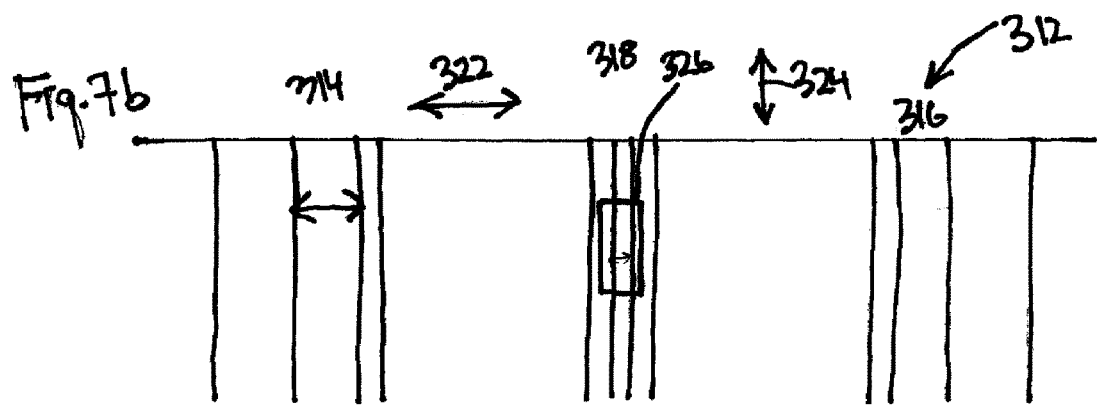

Further embodiments of a thinned out wall region in the sense of this application are shown with reference to FIG. 7. FIGS. 7*a* and 7*b* show a cross-section and a plan view of a wall region side of a component. In the cross-section of FIG. 7*a*, a component 300 having an inner wall 304 surrounding a flow region 302 is shown in the upper panel. The inner wall is produced in one piece from a metal block or by means of a sintering process and can, for example be an inlet tube of a blood pump. The inner wall has a substantially unchanging wall thickness of approximately 500 μm in a non-machined wall region 308. This wall thickness is reduced in a milled region 310 introduced on the wall region side 306. The milled region 310 comprises a thinned out wall region 312 that is shown enlarged in the middle panel.

The thinned out wall region 312 comprises three grooves 314, 316 and 318, with the grooves 314 and 316 being substantially arranged with mirror symmetry around a mirror axis extending through the middle groove 318, i.e. having a substantially corresponding shape. The wall thickness 320 is thinned out to approximately 100 μm within the grooves 314 and 316. The width of the groove amounts to approximately 250 μm to 2000 μm. The wall thickness increases again to approximately 400 μm at the right margin of the groove 314 and is no reduced up to the left margin of the middle groove 318 to approximately 100 μm. The wall thickness within the middle groove 318 amounts to approximately 35 μm and the groove has a width of approximately 100 μm in the transverse direction 322 (see lower panel of FIG. 7*a*). The groove 314 and the groove 316 are arranged with mirror symmetry about the middle groove 318 and are spaced approximately 800 μm apart from the middle groove 318.

The grooves 314, 316, and 318 effect a more sensitive measurement region for measuring the surface expansion in the groove 318. Although thinned out wall regions without grooves (as shown, for example, in FIG. 1*c*) have a high measurement sensitivity, the arrangement of FIG. 7*a* only requires a local thinning out of the wall thickness within the groove 318 to a region below 60 μm, while in the embodiment of FIG. 1*c*, the wall region side is essentially planar and the more material has to be removed. Even if the minimal wall thickness of the embodiment of FIG. 1*c* is reduced to approximately 35 μm, the stress maximum in the middle groove 318 is almost twice as much as in the wall geometry of FIG. 1*c*. The outer grooves 314 and 316 act as hinges to increase the stress maximum within the middle groove 318. The stress maximum can, however, also already be increased with only one groove in which the wall thickness has a non-disappearing, global minimum so that an individual groove on the wall region side in conjunction with a concave fluid region side forms an embodiment in accordance with the application.

A plan view of the thinned out wall region 312 is shown in FIG. 7*b*. The grooves 314, 316, and 318 extend substantially in parallel with the axial direction 324 of the component, in this case with the cylinder axis of the fluid conducting component 300. A section of a sensor for detecting the surface expansion is arranged within the middle groove 318 in the region 326.

Exemplary sensors for the detection of the surface expansion have already been presented in the preceding embodiments. However, use can also be made of the embodiments in accordance with FIG. 8.

Figure 8A:
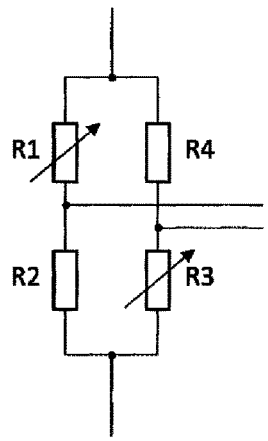
FIGS. 8a to 8d different sensor arrangements for detecting a surface expansion of the thinned out wall region.
Figure 8B:
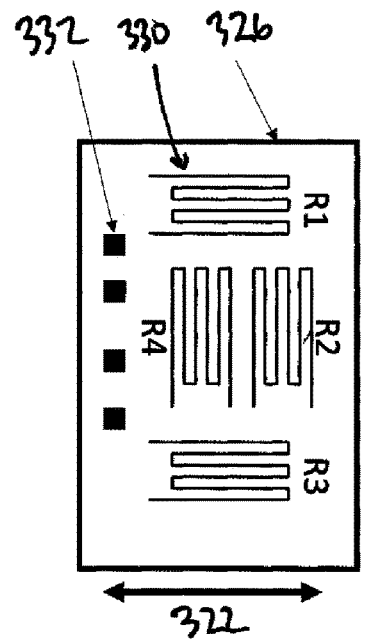
Figure 8C:
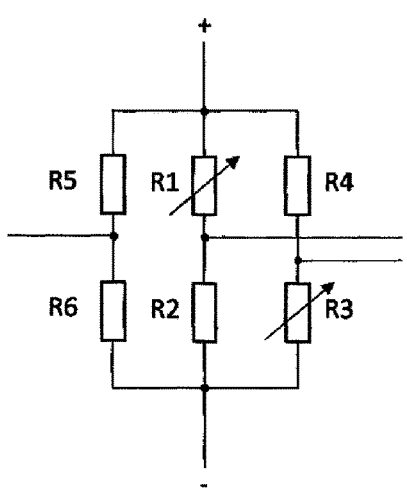

FIG. 8*a* shows an equivalent circuit diagram of the exemplary embodiment of the meander structures of FIG. 8*b* that can be arranged in the middle groove. The resistors R1 and R3 are changeable resistances, while the resistors R2 and R4 remain substantially unchanged under expansion in the transverse direction 322. The resistors R2 and R4 have the function of a temperature compensation and compensation of external influences such as radiation or aging. The four resistors R1 to R4 are formed as a half-bridge, as shown schematically in FIG. 8*a*.

The meander structures 330 shown in FIG. 8*b* are lithographically applied conductor tracks of a metal on an insulating substrate. In this respect, the long sides of the meanders of the resistors R1 and R3 extend along the transverse direction 322 and the long sides of the meanders of the resistors R2 and R4 extend along the axial direction 324. The meander structures are connected to contact pads 332, the contact pads to bond wires, with the bond wires being connected to further passive or active electronic components arranged on a printed circuit board, for example. Reference is made to the examples of FIGS. 3 to 6 for this purpose. The meander structures 330 of the resistors R1 and R3 are preferably designed the same, just like the meander structures 330 of the resistors R2 and R4. In other embodiments, the meander structures of the resistors R1 to R4 can be designed as identical (apart from the orientation of the meander structure in the transverse or axial direction).

Figure 8D:
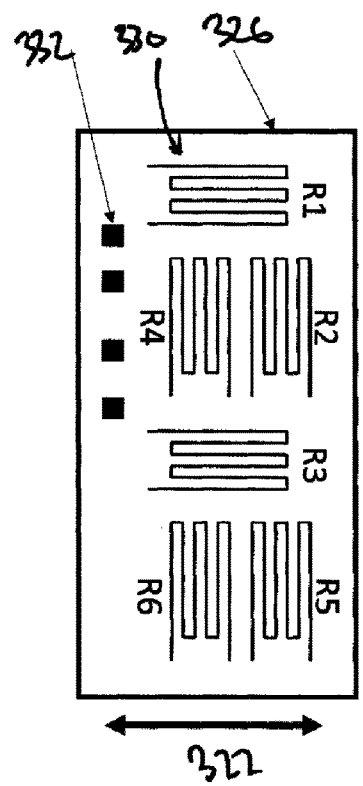

A further alternative of a sensor or of a sensor arrangement in the middle groove 318 is explained with reference to the equivalent circuit diagram 8*c* and exemplary meander structures in FIG. 8*d*. In this respect, a total of six resistors R1 to R6 are applied lithographically in the form of meander structures 330. The measurement bridge of FIGS. 8c and 8d here enables a simplified error correction with respect to the measurement bridge of FIGS. 8a and 8b since interference influences can be measured with the aid of the further resistors R5 and R6 and can subsequently be removed by calculation so that an exact comparison of the resistors and other elements of the sensor arrangement or of the sensor is no longer necessary.

Figure 9:
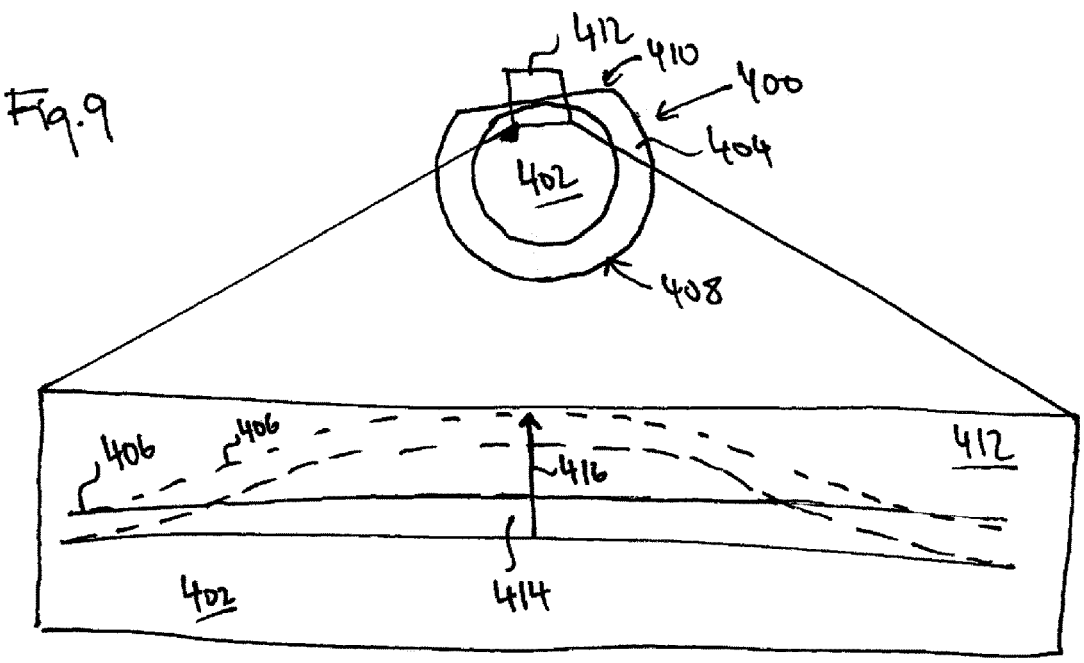
FIG. 9 a cross-section through a further exemplary thinned out wall region.

A further embodiment of a thinned out wall region is shown in FIG. 9. Here, the upper panel of FIG. 9 shows a component 400, for example an inlet tube of a blood pump. A fluid region 402 is bounded by an inner wall 404. The fluid region here has a cylindrical shape or a sectionally cylindrical shape. The inner wall comprises a region 408 having a substantially unchanging wall thickness and a region 410 having a reducing wall thickness, with the thinned out region 412 being shown schematically in the lower panel. The reducing wall thickness is effected by a milling of the wall region side 406 in the region 410. In this respect, the wall thickness 412 can have a minimum of approximately 30 µm. The wall thickness in the region of unchanging wall thickness is comparable with the embodiment of FIG. 7.

The thinned out wall region is shown in two different states in the lower panel of FIG. 9. In the first state, that is shown by the solid lines, the pressure present in the fluid region is equal to the pressure present between the inner wall and the outer wall, i.e. the pressure difference between the fluid region side and the wall region side is zero. The second state, that is shown by dashed lines, shows a pressure difference between the fluid region and the wall region side, with the pressure being higher in the fluid region. Due to the increased pressure, the thinned out wall region in the region 414 of its minimal wall thickness is raised radially outwardly by a stroke height 416. An exemplary stroke can, for example, amount to 2 µm at 750 mmHg.

Figure 10A:
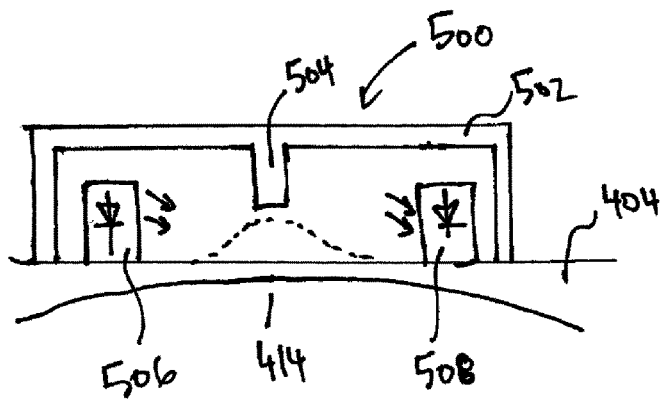
FIGS. 10a to 10c exemplary sensor arrangements.

This stroke height can be detected and evaluated in different manners. The stroke height can here be used, for example, as a measure of the pressure difference. In FIG. 10a, an optical sensor arrangement 500 for detecting the stroke height is shown. The sensor arrangement comprises a preferably opaque housing 502 that is arranged on the wall region side 406 and that has a web 504 that extends in a radial extension of the minimum of the wall thickness from the inner housing side in the direction of the wall region side. The sensor arrangement further comprises a light emitting diode 506 and a photosensor 508 that are arranged on different sides of the web 504. At a pressure difference of zero, the photosensor receives an unchanging luminosity. If an excess pressure is present on the fluid region side, the inner wall is raised in the region of the minimal wall thickness (drawn dashed) so that the luminosity received at the photosensor is reduced. The pressure difference that occurs can be quantitatively determined from this by means of a calibration procedure.

Figure 10B:
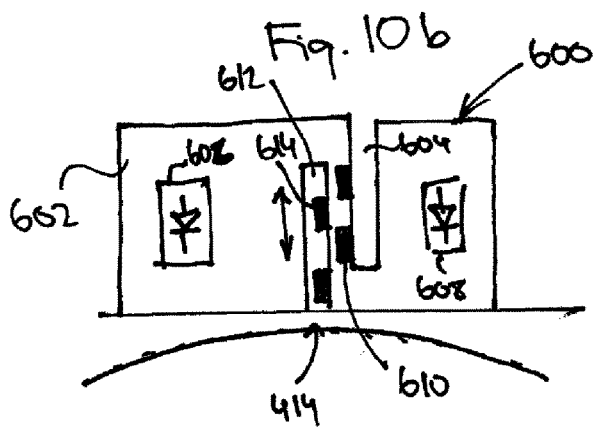

An alternative sensor arrangement 600 is shown in FIG. 10b. In a similar manner to the sensor arrangement 500, the sensor arrangement 600 has an opaque housing 602 having a photocell 606 arranged therein and a photocell 608 as a receiver. A web 604 is furthermore arranged in the housing that, unlike the web 504, is, however, at least light permeable. Sections 610 impermeable to light are arranged on the web. A further web 612 that is likewise light permeable and that likewise has sections 614 impermeable to light is located in the region 414 of minimal wall thickness. The sections 610 and 614 impermeable to light are oriented with respect to one another with a pressure difference of zero such that only a little light of the photocell 606 reaches the receiver 608. In the case of a pressure difference, the web 612 directly arranged on the membrane is displaced due to the wall or membrane stroke and light permeable gaps become free so that the receiver 608 now receives more light. The light permeable regions of the webs 604 and 612 therefore form an example of a diffractive grating.

Figure 10C:
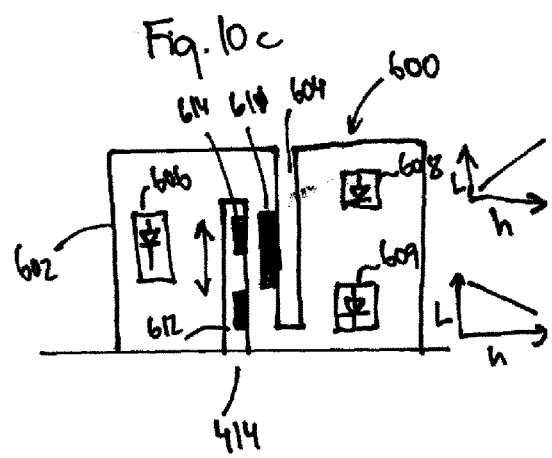

A further alternative sensor arrangement results when two receivers 608 and 609 are provided instead of the one receiver 608. In this case, the two receivers can form a differential amplifier when the sections on the webs 604 and 612 impermeable to light are correspondingly selected. With a pressure difference of zero, for example, the receiver 608 can thus receive the full illumination amount L of the photocell 606, whereas the receiver 609 only receives a minimal illumination amount L. For this purpose, the elements 610 impermeable to light can be arranged, for example, in this manner as an individual element 611. On a corresponding stroke, the illumination amount L at the receiver 608 then drops and increases accordingly at the receiver 609 (see the right panel of FIG. 10c). In other embodiments, not shown, interference effects can also be detected at a diffractive grating.

Further sensor arrangements for evaluating a pressure-induced stroke of the thinned out wall region are explained with reference to FIG. 11. Here, a state with a pressure difference Δp of zero is shown in the left panel and a state with an excess pressure Δp>0 is shown in the region at the fluid region side that effects a radially outwardly directed stroke of the wall region having a minimal wall thickness.

FIG. 11a shows a sensor arrangement that is based on a mirror galvanometer. In this respect, a mirror 700 is applied in the region of the minimal wall thickness 414. The mirror is irradiated by means of a coherent light source 702 such as by means of a diode laser and reflects the light onto a multipixel image sensor 704. In the case of a pressure difference (see right panel), different pixels are irradiated.

FIG. 11b shows an arrangement for determining the stroke by means of an alternative optical sensor. Here, a lens 712 and, for example, an oil film 714 are located between the wall region side of the inner wall 404 in the region of the smallest wall thickness 414 and a projection system 710. An image sensor 716 is located above the projection system. In the case of a pressure-induced stroke, height changes in the oil film occur that are caused by the pressure, with these changes being visible in the form of Fresnel rings and being able to be evaluated.

FIG. 11c shows a sensor arrangement that comprises a speckle interferometer. A laser 720, a semitransparent mirror 722, and a fully reflective mirror 724, as well as a projection system 726 and an image sensor 728 are essentially used here. Depending on the change of the stroke, speckle patterns that change in dependence on the stroke become visible on a sensor arranged above the region of minimal wall thickness 414. The laser acts as a reference light source here.

FIG. 11d does not show an optical sensor, but rather a resistive sensor in the form of a piezo sensor. Different strokes of a varying current or of a varying resistance are measured here (see right panel). A conductive membrane (or a thinned out wall region) is used for particularly accurate measurements or a conductive layer is applied to the membrane. A piezo element 730 is arranged such that an electrical contact between a contact element 732 and the conductive membrane layer 734 can be established or interrupted. A tunneling current can be measured between the contact elements in the transition region between the states "contacted" and "interrupted". This tunneling current is very sensitive to distance changes. The piezo crystal is now controlled such that a constant tunneling current is adopted. The required voltage at the piezo crystal is a measure for the deformation and thus for the measured pressure.

FIG. 11e shows a piezo scanning unit with a capacitive evaluation. In this respect, the piezo unit is covered by a capacitor plate above the region of minimal wall thickness so that strokes enable an evaluation by the capacitor, comprising the upper side of the piezo element 740 and the capacitor plate 742. The control of the piezo element is, as in FIG. 11d, such that a constant tunneling current is adopted. The advantage in comparison with the setup in FIG. 11d comprises hysteresis and aging effects of the piezo element being suppressed.

Further embodiments and examples result for the skilled person in an obvious manner.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The application inter alia comprises the following aspects:
1. A component for conducting a fluid having a sensor (100), wherein the component comprises an inner wall (4) and an outer wall, wherein the inner wall (4) is configured to conduct the fluid, the outer wall terminates the component to the outside, and a wall region is formed between the inner wall (4) and the outer wall, characterized in that
    the sensor (100) has an electromechanical sensor element (2) and is arranged in the wall region at the inner wall (4); wherein
    the sensor (100) is adapted to measure a degree of deformation of the inner wall (4) in the region of the sensor (100) by means of the sensor element (2) and to output it as an electrical signal, with
    the electromechanical sensor element (2) preferably having a length and/or preferably a width of ≤50 µm.
2. A component in accordance with the preceding aspect, characterized in that the sensor has two electrical contacts and the sensor element is a nanostructural expansion element that is applied materially integral to the contacts so that the contacts electrically contact one another via the sensor element, with the electrical contacts being applied to the inner wall such that the sensor element deforms with the inner wall on a deformation of the inner wall in the region of the sensor so that the electrical signal is measurable between the electrical contacts.
3. A component in accordance with the preceding aspect, characterized in that a plurality of sensors (100) are arranged in the wall region at the inner wall (4), in particular in that four sensors (100) are arranged that are connected to one another to form a full bridge or half-bridge circuit to reduce a temperature dependence of the sensors (100).
4. A component in accordance with one of the preceding aspects, characterized in that an insulation layer (5) that is connected materially integral to the inner wall (4) and the electrical contacts (1) is arranged between the inner wall (4) and the electrical contacts (1) of the sensor (100).
5. A component in accordance with one of the preceding aspects, characterized in that the electrical signal includes a change of electrical resistance of the sensor (100).
6. A component in accordance with one of the preceding aspects, characterized in that the sensor element (2) has a length and/or a width of ≤15 µm, in particular ≤10 µm, in particular ≤3 µm, and/or a thickness of ≤50 µm, in particular ≤15 µm, in particular ≤10 µm, in particular ≤3 µm.
7. A component in accordance with one of the aspects 2 to 6, characterized in that the electrical contacts (1) are applied to the inner wall (4) such that there is a gap (3) between the contracts (1) of ≤50 µm, in particular ≤15 µm, in particular ≤10 µm, in particular ≤3 µm, with the gap (3) being completely covered by the sensor element (2) in a transverse direction.
8. A component in accordance with one of the preceding aspects, characterized in that the sensor is arranged in a thinned region of the inner wall.
9. A component in accordance with one of the preceding aspects, characterized in that electrical connection elements are arranged in the wall region via which the sensor is connected to a processing device.
10. A component in accordance with the preceding aspect, characterized in that the connection elements comprise a printed circuit board (20), with one or more sensors (100) being directly connected to the printed circuit board (20) via the electrical contact (1) or via bond wires or individually insulated leads, in particular Teflon insulated leads.
11. A component in accordance with the preceding aspect, characterized in that electrical components (22) are arranged on the printed circuit board (20) for the preprocessing of the electrical signals, in particular for pre-amplification.
12. A method of manufacturing a component for conducting a fluid having a sensor (100) comprising:
    forming an inner wall (4) and an outer wall of the component, wherein the inner wall (4) is configured to conduct the fluid and the outer wall is configured to terminate the component to the outside and to join the inner wall (4) and the outer wall together such that a wall region is produced between the inner wall (4) and the outer wall;
    arranging a sensor (100) having an electromechanical sensor element (2) in the wall region at the inner wall (4), wherein the sensor (100) is adapted to measure a degree of deformation of the inner wall (4) in the region of the sensor (100) by means of the sensor element (2) and to output it as an electrical signal, with the electromechanical sensor element (2) preferably having a length and/or preferably having a width of ≤50 µm; and
    joining the inner wall (4) and the outer wall together.
13. A method in accordance with the preceding claim, characterized in that an insulation layer (5) is applied to the inner wall (4) in the wall region prior to the arrangement of the sensor (100).

14. A method in accordance with one of the two preceding aspects, characterized in that the arrangement of the sensor (100) comprises:
applying two electrical contacts (1) in the wall region onto the inner wall (4) or onto the insulation layer (5) for picking up the electrical signal;
applying the sensor element (2) to the electrical contacts (1).

15. A method in accordance with the preceding aspect, characterized in that the sensor element (2) is applied to the contacts (1) by means of nano 3D printing, sputtering, or by means of an etching process.

16. A component in accordance with one of the aspects 1 to 11, wherein a fluid region side of the inner wall is concave and the sensor is arranged on a wall region side in a region of minimal thickness of the inner wall.

17. A component in accordance with one of the aspects 1 to 11, wherein a fluid region side of the inner wall is concave and a wall region side has at least one groove in which the sensor is arranged.

18. A component in accordance with aspect 17, wherein at least three grooves are present and the sensor is arranged in the middle groove.

19. A component in accordance with one of the aspects 1 to 11 or 15 to 17, wherein the sensor is configured such that a raising of the inner wall in the region of the sensor is detected by the sensor.

20. A component in accordance with one of the aspects 1 to 11 or 15 to 18, wherein the sensor is an optical, resistive, or capacitive sensor.

The invention claimed is:

1. A component for conducting a fluid having a sensor, wherein the component comprises an inner wall and an outer wall, wherein the inner wall is configured to conduct the fluid, the outer wall terminates the component to the outside, and a wall region is formed between the inner wall and the outer wall,
wherein
the sensor has an electromechanical sensor element and is arranged in the wall region at the inner wall; wherein
the sensor is adapted to measure a degree of deformation of the inner wall in the region of the sensor by means of the sensor element and to output it as an electrical signal, wherein the sensor is arranged in a region of minimal wall thickness of the inner wall and a fluid region side is concave in this region.

2. The component of claim 1, wherein the sensor has two electrical contacts and the sensor element is a nanostructural expansion element that is applied materially integral to the contacts so that the contacts are electrically contacted with one another via the sensor element, with the electrical contacts being applied to the inner wall such that the sensor element deforms with the inner wall on a deformation of the inner wall in the region of the sensor so that the electrical signal is measurable between the electrical contacts.

3. The component of claim 1, wherein a plurality of sensors are arranged in the wall region at the inner wall; in that four sensors are arranged that are connected to one another to form a full bridge or half-bridge circuit to reduce a temperature dependence of the sensors.

4. The component of claim 1, wherein an insulation layer that is connected materially integral to the inner wall and the electrical contacts is arranged between the inner wall and the electrical contacts of the sensor.

5. The component of claim 1, wherein the electrical signal includes a change of electrical resistance of the sensor.

6. The component of claim 2, wherein the sensor element has a length and/or a width of ≤50 µm, and/or a thickness of ≤50 µm.

7. The component of claim 6, wherein the electrical contacts are applied to the inner wall such that there is a gap between the contacts of ≤50 µm, with the gap being completely covered by the sensor element in a transverse direction.

8. The component of claim 1, wherein the sensor is arranged in a thinned region of the inner wall.

9. The component of claim 1, wherein electrical connection elements are arranged in the wall region via which the sensor is connected to a processing device.

10. The component of claim 1, wherein the connection elements comprise a printed circuit board, with one or more sensors being directly connected to the printed circuit board via the electrical contacts or via bond wires or individually insulated Teflon leads.

11. The component of claim 1, wherein electrical components are arranged on the printed circuit board for the preprocessing of the electrical signals.

12. The component of claim 1, wherein a fluid region side of the inner wall is concave and a wall region side has at least one groove in which the sensor is arranged.

13. The component of claim 12, wherein at least three grooves are present and the sensor is arranged in the middle groove.

14. The component of claim 1, wherein the sensor is configured such that a raising of the inner wall in the region of the sensor is detected by the sensor.

15. The component of claim 13, wherein the sensor is an optical, resistive, or capacitive sensor.

* * * * *